United States Patent
Hunt

(10) Patent No.: US 12,186,166 B2
(45) Date of Patent: Jan. 7, 2025

(54) HEAT-ASSISTED PUMPING SYSTEMS FOR USE IN NEGATIVE PRESSURE WOUND THERAPY

(71) Applicant: Smith & Nephew PLC, Watford (GB)

(72) Inventor: Allan Kenneth Frazer Grugeon Hunt, Beverley (GB)

(73) Assignee: Smith & Nephew PLC, Watford (GB)

( * ) Notice: Subject to any disclaimer, the term of this patent is extended or adjusted under 35 U.S.C. 154(b) by 453 days.

(21) Appl. No.: 17/385,651

(22) Filed: Jul. 26, 2021

(65) Prior Publication Data

US 2022/0000672 A1 Jan. 6, 2022

Related U.S. Application Data

(63) Continuation of application No. 15/574,793, filed as application No. PCT/EP2016/061147 on May 18, 2016, now Pat. No. 11,071,653.

(Continued)

(51) Int. Cl.
*A61F 13/05* (2024.01)
*A61M 1/00* (2006.01)
(Continued)

(52) U.S. Cl.
CPC .............. *A61F 13/05* (2024.01); *A61M 1/80* (2021.05); *A61M 1/962* (2021.05); *F01B 3/007* (2013.01);
(Continued)

(58) Field of Classification Search
CPC .......... A61M 1/00; A61M 27/00; A61M 1/80; A61M 1/962; A61M 1/60; A61M 2205/36; A61M 2205/3606; A61M 2205/3613; A61M 2205/362; A61M 2205/3646; A61M 2205/366; A61M 2205/3693; A61F 13/00;
(Continued)

(56) References Cited

U.S. PATENT DOCUMENTS 3,788,772 A 1/1974 Noble et al.
3,947,156 A * 3/1976 Becker .................... F04B 45/04
92/99

(Continued)

FOREIGN PATENT DOCUMENTS

CN 102102655 B * 6/2014 .............. F04B 43/02
EP 1051984 A2 11/2000
(Continued)

OTHER PUBLICATIONS

American Heritage definition for "bellows." Accessed Jul. 26., 2024 https://www.ahdictionary.com/word/search.html?q=bellows (Year: 2024).*

(Continued)

*Primary Examiner* — Adam Marcetich
(74) *Attorney, Agent, or Firm* — Knobbe, Martens, Olson & Bear, LLP

(57) ABSTRACT

A device and method for treating a wound of a patient with negative pressure is provided. The device comprises a heat-assisted pump system. The pump system can be powered in part by heat derived from the patient. The pump system may be configured to be highly planar, light weight, and portable. The pump system may comprise a Stirling engine or a thermal acoustic engine.

18 Claims, 5 Drawing Sheets

Related U.S. Application Data

(60) Provisional application No. 62/163,268, filed on May 18, 2015.

(51) Int. Cl.
| | |
|---|---|
| *F01B 3/00* | (2006.01) |
| *F01B 23/08* | (2006.01) |
| *F02G 1/043* | (2006.01) |
| *F03G 3/00* | (2006.01) |
| *F03G 7/00* | (2006.01) |
| *F04B 17/00* | (2006.01) |
| *F04B 45/033* | (2006.01) |
| *F04B 45/053* | (2006.01) |

(52) U.S. Cl.
CPC ............ *F01B 23/08* (2013.01); *F02G 1/0435* (2013.01); *F03G 3/00* (2013.01); *F03G 7/002* (2013.01); *F04B 17/00* (2013.01); *F04B 45/033* (2013.01); *F04B 45/053* (2013.01); *A61M 1/60* (2021.05); *A61M 2205/36* (2013.01); *A61M 2205/3606* (2013.01); *A61M 2205/3613* (2013.01); *A61M 2205/362* (2013.01); *A61M 2205/3646* (2013.01); *A61M 2205/366* (2013.01); *A61M 2205/3693* (2013.01); *F02G 2243/54* (2013.01); *F02G 2270/20* (2013.01); *F02G 2280/50* (2013.01)

(58) Field of Classification Search
CPC .... A61F 13/02; A61F 15/00; A61F 13/00068; A61F 13/0216; F01B 3/00; F01B 3/007; F01B 23/08; F02G 1/04; F02G 1/0435; F02G 2243/54; F02G 2270/20; F02G 2280/50; F04B 17/00; F04B 45/033; F04B 45/053; F03G 3/00; F03G 7/002
See application file for complete search history.

(56) References Cited

U.S. PATENT DOCUMENTS

| | | | | |
|---|---|---|---|---|
| 4,483,666 A | * | 11/1984 | Schubert ............ | F04B 43/1207 417/474 |
| 4,634,430 A | | 1/1987 | Polaschegg | |
| 5,354,268 A | * | 10/1994 | Peterson ................ | A61M 1/74 604/35 |
| 5,458,469 A | * | 10/1995 | Hauser ................ | F04B 43/1207 417/474 |
| 5,533,886 A | * | 7/1996 | Von Der Heyde .. | F04B 43/1207 418/45 |
| 6,142,982 A | * | 11/2000 | Hunt ....................... | A61M 1/82 604/313 |
| 8,829,263 B2 | * | 9/2014 | Haggstrom ....... | A61F 13/00068 602/53 |
| 2001/0019344 A1 | * | 9/2001 | Harada ............... | F04B 43/1207 347/85 |
| 2004/0204679 A1 | * | 10/2004 | Visconti .............. | A61M 3/0201 604/131 |
| 2006/0149170 A1 | * | 7/2006 | Boynton ................. | A61M 1/80 601/7 |
| 2007/0078366 A1 | * | 4/2007 | Haggstrom ......... | A61F 13/0203 602/53 |
| 2007/0265586 A1 | * | 11/2007 | Joshi ....................... | A61M 1/78 604/313 |
| 2008/0103462 A1 | | 5/2008 | Wenzel et al. | |
| 2008/0306456 A1 | * | 12/2008 | Riesinger ............ | A61F 13/0203 604/316 |
| 2009/0165640 A1 | * | 7/2009 | Kawasaki ............... | F04B 45/02 91/169 |
| 2009/0227969 A1 | * | 9/2009 | Jaeb ....................... | A61M 1/985 604/313 |
| 2009/0299306 A1 | | 12/2009 | Buan | |
| 2011/0028918 A1 | * | 2/2011 | Hartwell ............. | A61F 13/0226 604/319 |
| 2011/0112492 A1 | * | 5/2011 | Bharti ..................... | A61F 13/05 604/319 |
| 2011/0282310 A1 | | 11/2011 | Boehringer et al. | |
| 2012/0184890 A1 | * | 7/2012 | Rastegar ................. | A61L 15/14 602/53 |
| 2013/0042753 A1 | * | 2/2013 | Becker ................ | F04B 43/0054 92/96 |
| 2014/0003983 A1 | * | 1/2014 | Roach .................... | F04B 43/02 417/472 |
| 2014/0343518 A1 | * | 11/2014 | Riesinger .............. | A61M 1/964 604/319 |
| 2015/0057625 A1 | * | 2/2015 | Coulthard .............. | B65D 75/30 604/319 |
| 2015/0202354 A1 | * | 7/2015 | Wall ...................... | A61F 13/022 604/319 |

FOREIGN PATENT DOCUMENTS

| | | |
|---|---|---|
| EP | 2216057 A2 | 8/2010 |
| RU | 2417110 C2 * | 4/2011 |
| WO | WO-2008100440 A1 | 8/2008 |
| WO | WO-2013151089 A1 | 10/2013 |
| WO | WO-2015123609 A1 | 8/2015 |
| WO | WO-2015200731 A2 | 12/2015 |

OTHER PUBLICATIONS

Merriam Webster definition for "bellows." Accessed Jul. 26., 2024 https://www.merriam-webster.com/dictionary/bellows (Year: 2024).*
Your Dictionary definition for "bellows." Accessed Jul. 26., 2024 https://www.yourdictionary.com/bellows (Year: 2024).*
International Search Report and Written Opinion for Application No. PCT/EP2016/061147, mailed on Oct. 6, 2016, 18 pages.

* cited by examiner

HEAT-ASSISTED PUMPING SYSTEMS FOR USE IN NEGATIVE PRESSURE WOUND THERAPY

CROSS-REFERENCE TO RELATED APPLICATIONS

This application is a continuation of U.S. patent application Ser. No. 15/574,793, filed Nov. 16, 2017, which is a U.S. national stage application of International Patent Application No. PCT/EP2016/061147, filed May 18, 2016, which claims priority to U.S. Provisional Patent Application No. 62/163,268, filed on May 18, 2015.

BACKGROUND OF THE INVENTION

Field

This application is directed to systems and methods for treating a wound with topical negative pressure (TNP) therapy. Embodiments disclosed relate to pump systems and wound dressings for use in TNP therapy.

Background

Many different types of wound dressings are known for aiding the healing process of a human or animal wound. These different types of wound dressings include many different types of materials and layers, for example, gauze pads, foam pads, absorbent layers, breathable layers, adhesive layers and non-adhesive layers.

Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like. TNP therapy assists in the closure and healing of wounds by reducing tissue edema; encouraging blood flow; stimulating the formation of granulation tissue; removing excess exudates, and may reduce bacterial load and thus reduce the potential for infection of the wound. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability. TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system for providing negative pressure to a wound site. Wound treatment apparatuses may also comprise wound dressings that may be used in combination with the pump systems described herein, and connectors for connecting the wound dressings to the pump systems.

In accordance with one embodiment, a pump system is provided. The pump system comprises a first member and a second member, the first member having a higher temperature than the second member. The pump system utilizes the heat differential between the first and second members to drive or assist the pump system in generating a vacuum pressure, thereby extending the portability and operational duration of the pump system.

In one aspect of the invention, the pump system comprises a Stirling engine with a generally planar configuration. The Stirling engine comprises a canted swash plate disposed between a hot plate and a cold plate.

Optionally, a vacuum pressure is generated by the compression of one or more bellows by the movement of the swash plate.

In one aspect of the invention, the pump system comprises a thermal acoustic engine. The thermal acoustic engine is configured to transform the sound wave generated by the thermal acoustic engine into a vacuum pressure that can be applied to the wound.

Optionally, the thermal acoustic engine comprises a diaphragm configured to move in response to the sound wave generated by the thermal acoustic engine.

Optionally, the pump system comprises a canister to receive the wound exudate.

DETAILED DESCRIPTION

Figure 1:
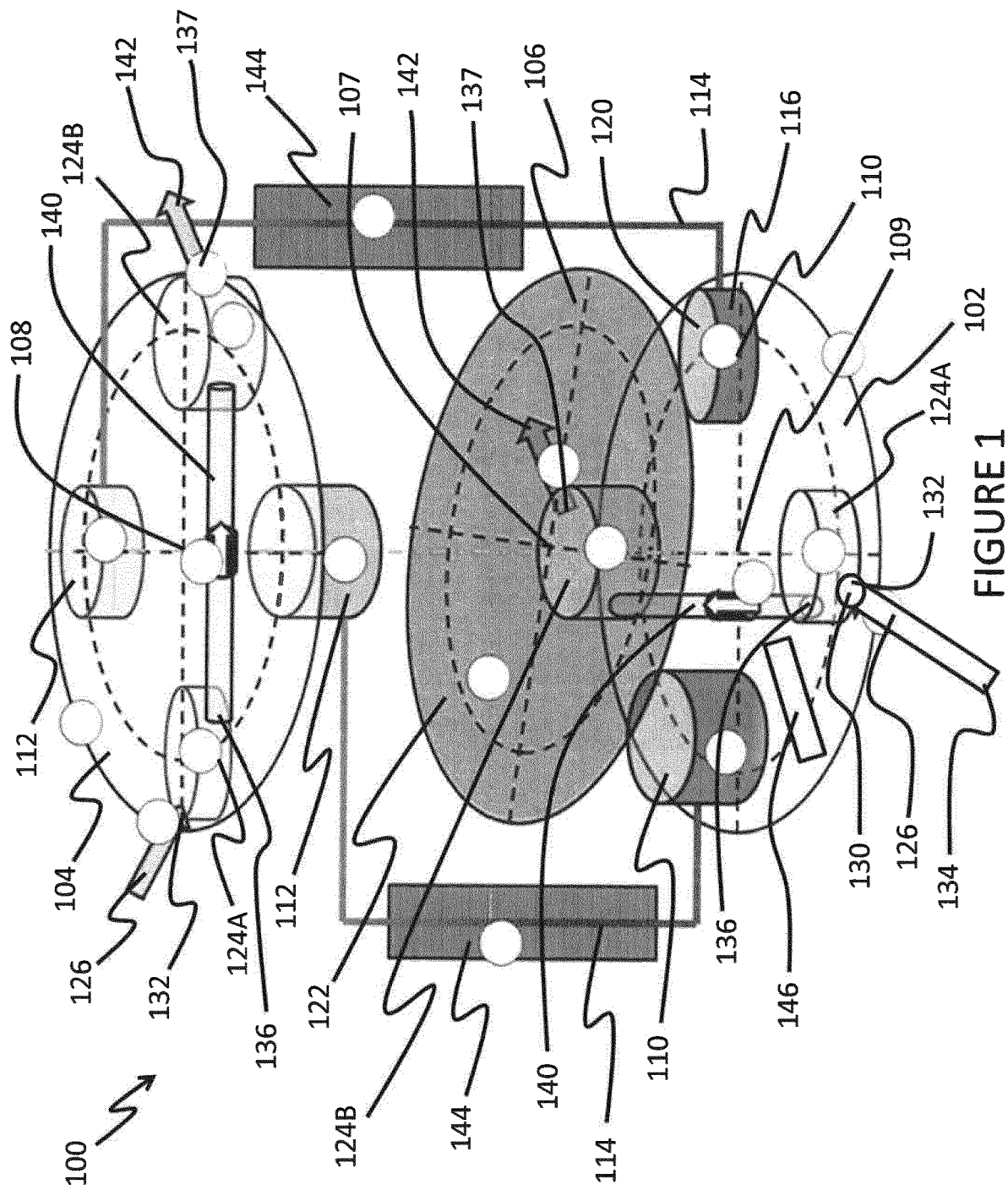
FIG. 1 shows a schematic perspective view of a pump system comprising a Stirling engine.

It will be understood that embodiments of the present disclosure are generally applicable for use in TNP therapy systems. Briefly, negative pressure wound therapy assists in the closure and healing of many forms of "hard to heal" wounds by applying a negative pressure to the wound site. Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

Many wound dressings used in TNP therapy employ a pump system to generate a negative pressure at the wound site. Bulky or heavy pump systems compromise the portability of a TNP wound therapy system. On the other hand, small or light-weight pumping systems may have a limited ability to operate for a significant amount of time or may have a limited ability to deliver substantial negative pressures to the wound site. One challenge associated with designing wound dressings for use in TNP therapy is achieving a portable dressing that can supply adequate negative pressure to the wound for a substantial amount of time. A device that can be mounted on a dressing has not yet been devised that can operate for a commercially suitable length of time. Devices under 50 cubic centimeters usually have upper operational durations of under two weeks. Devices with 60-day operation capability may be bulky or require recharging.

The novel systems disclosed herein enable portable wound dressings for TNP wound therapy. Many of the disclosed embodiments provide pumping systems that have a long operational duration and are suitable for use in TNP wound therapy. In some embodiments, energy derived from the patient is used, at least in part, to assist or drive the pumping system that generates the negative pressure at the wound site. In some embodiments, the pump system can be included as part of a wound treatment apparatus which can include, for example, a wound dressing. Although not required, embodiments of the wound dressings herein disclosed can be sterile.

In some embodiments, the pump system can be separate from the wound dressing as a standalone unit. This can beneficially allow the pump system to be positioned at a different location away from the wound dressing. In some embodiments, the pump system can be attached to (e.g., incorporated in) the wound dressing to form a single unit. This can potentially reduce the form factor of the wound treatment apparatus and reduce the length of a conduit attaching the pump system to the wound dressing.

In some embodiments, the pump system can operate in a canisterless system, in which the wound dressing retains exudate aspirated from the wound. Such a dressing can include a filter, such as a hydrophobic filter, that prevents passage of liquids downstream of the dressing (toward the pump system). In other embodiments, the pump system can operate in a system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments disclosed herein, the components of the TNP system described herein can be particularly suited for incisional wounds that exude a small amount of wound exudate.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The operating negative pressure range for some embodiments of the present disclosure can be between approximately −10 mmHg to −200 mmHg, between −20 mmHg to −150 mmHg, between −45 mmHg to −100 mmHg, any subrange within these ranges, or any other range as desired.

The pump system embodiments described herein can have a compact, small size. The diameter of the Stirling engine pump herein disclosed can be between approximately 5 mm to 400 mm, between 10 mm to 200 mm, between 20 mm to 100 mm, any subrange within these ranges, or any other range desired. The thickness of the Stirling engine pump herein disclosed can be between approximately 1 mm to 30 mm, between 2 mm to 20 mm, between 3 mm to 10 mm, any subrange within these ranges, or any other range desired. The thermoacoustic path lengths for the pump systems herein disclosed can be between approximately 1 mm to 150 mm, between 2 mm to 100 mm, between 3 mm to 50 mm, any subrange within these ranges, or any other range desired. By way of a non-limiting example, the thermoacoustic path length can range from 3.3 mm for a quarter wave oscillator to run at 26 kHz up to around 50 mm.

In some embodiments, the pump system uses a Stirling engine to drive or assist a pumping system that generates a negative pressure at the wound site. Stirling engines are a method of harnessing energy from a hot heat exchanger. Generally, Stirling engines use cyclic compression and expansion of an enclosed fluid (often called "the working fluid") to drive the displacement of a piston. Because the working fluid is enclosed, Stirling engines may be powered by a variety of hot heat exchangers.

A Stirling engine includes generally includes two volumes that are fluidically connected to one another. One of the volumes contains working fluid that is at a high temperature, while the working fluid in the other volume is kept at a low temperature. A cycle of a Stirling engine comprises two phases, herein referred to as (1) a power stroke and (2) a compression phase. During the power stroke phase, the working fluid in the hot volume pushes against a drive piston, causing the drive piston to move in the direction of the applied force. Mechanical work (which is the product of a force and a displacement in the direction of the force) is done during the power stroke of the Stirling engine cycle. During the compression phase, the drive piston is moved back to compress the working fluid in the hot volume, thereby resetting the drive piston for another cycle of the engine.

Stirling engines have been designed in several configurations (e.g., alpha, beta). Stirling engines often use a rotational crank as either the output drive or as an intermediate state. Additionally, Stirling engines tend to have a tall form factor when the crank mechanism is included. For incorporating into a wound dressing, Stirling engines having a planar configuration may be beneficial.

FIG. 1 depicts one embodiment of a pump system 100 that can include a Stirling engine. The pump system 100 may be used for TNP therapy. In some embodiments the pump system 100 can be incorporated into a portable wound dressing. In many embodiments, the pump system 100 can be planar and suitable for use in TNP therapy wound dressing.

In some embodiments, the pump system 100 can have a hot plate 102 thermally connected to a hot heat exchanger. A cold plate 104 can be thermally connected to a cold heat exchanger and separated from the hot plate 102 by a distance. In some embodiments, the hot plate 102 can receive at least a portion of its heat from the patient (e.g., the hot plate 102 can be in direct or indirect contact with the patient).

A swash plate 106 can be disposed between the hot plate 102 and the cold plate 104. In some embodiments, the swash plate 106 can be canted so that a portion of the swash plate 106 is closer to the cold plate 104 than to the hot plate 102 while a different portion of the swash plate 106 is closer to the hot plate 102 than to the cold plate 104. In at least one embodiment, the swash plate 106 can pivot about its center 107 so that the point of the swash plate 106 that is closest to the hot plate 102 moves continuously around the circumference of the hot plate 102.

The hot plate 102 can have a hot cylinder 110 that is thermally coupled to the hot plate 102. Similarly, the cold plate 104 can have a cold cylinder 112 that is thermally coupled to the cold plate 104. The hot cylinder 110 and the cold cylinder 112 can be fluidically connected to one another by a connecting line 114.

A working fluid 116 can be contained within the closed system formed by the hot cylinder 110, the cold cylinder 112, and the connecting line 114. In some embodiments, the hot cylinder 110 can be bounded on one side by the hot plate 102 and on an opposing side by a drive piston 120. In some embodiments, the drive piston 120 can include a portion of the swash plate 106. In some embodiments, the drive piston 120 can be coupled to the swash plate 106 by an intermediate linkage (not shown). In some embodiments, the drive piston 120 can move within the hot cylinder 110. In some embodiments, the hot cylinder 110 can be a flexible bladder (e.g., bellows) that is sandwiched between the swash plate 106 and the hot plate 102.

The cold cylinder 112 can be bounded on one side by the cold plate 104 and on an opposing side by a cold piston 122. In some embodiments, the cold piston 122 can include a portion of the swash plate 106. In some embodiments, the cold piston 122 can be coupled to the swash plate 106 by a linkage (not shown). In some embodiments, the cold piston 122 can move within the cold cylinder 112. In some embodiments, the cold cylinder 112 can be a flexible bladder (e.g., bellows) that is sandwiched between the swash plate 106 and the cold plate 104.

In some embodiments, at the beginning of the power stroke phase, the drive piston 120 can compress the working fluid 116 within the hot cylinder 110, driving some of the working fluid 116 through the connecting line 114 and into the cold cylinder 112. As heat is added to the hot cylinder 110 through the hot plate 102, the working fluid 116 within the hot cylinder 110 can expand. The expansion of the working fluid 116 can force the drive piston 120 away from the hot plate 102, causing the swash plate 106 to pivot. In some embodiments, the movement of the drive piston 120 away from the hot plate 102 can draw some of the working fluid 116 from the cold cylinder 112, through the connecting line 114 and into the hot cylinder 110. In some embodiments, movement of the drive piston 120 can cause the swash plate 106 to compress the cold cylinder 112, causing some of the working fluid 116 in the cold cylinder 112 to flow through the connecting line 114 and into the hot cylinder 110. In at least one embodiment, the flow of the working fluid 116 from the cold cylinder 112 into the hot cylinder 110 can be the result of both the movement of the drive piston 120 drawing in the working fluid 116 and the movement of the swash plate 106 squeezing the working fluid 116 out of the cold cylinder 112.

The working fluid 116 in the cold cylinder 112 can be at a lower temperature than the working fluid 116 within the hot cylinder 110. At the beginning of the compression phase of the engine cycle, the infusion of the working fluid 116 from the cold cylinder 112 into the hot cylinder 110 can reduce the temperature of the working fluid 116 within the hot cylinder. At the end of the power stroke phase, the swash plate 106 can continue to move due to the momentum imparted to the swash plate 106 by the drive piston 120 during the power stroke phase of the cycle. In some embodiments, the momentum imparted to the swash plate 106 can cause the swash plate 106 to pivot in a rolling fashion. In some embodiments, the momentum imparted to the swash plate 106 can cause the swash plate 106 to tilt back and forth.

As the swash plate 106 moves, the swash plate 106 can return the drive piston 120 toward the hot plate 102. In some embodiments, the swash plate 106 can be configured so that movement of the swash plate 106 draws the cold piston 122 away from the cold plate 104, causing the working fluid 116 to be drawn from the hot cylinder 110, through the connecting line 114, and into the cold cylinder 112. In at least one embodiment, the flow of the working fluid 116 from the hot cylinder 110 into the cold cylinder 112 can be the result of both the movement of the swash plate 106 drawing the working fluid 116 into the cold cylinder 112 and the movement of the swash plate 106 squeezing the working fluid 116 out of the hot cylinder 110.

The mixing of colder working fluid 116 from the cold cylinder 112 with hotter working fluid 116 in the hot cylinder 110 can reduce the temperature of the working fluid 116 within the hot cylinder 110. The pressure of a given volume of gas is inversely related to the temperature of the gas. Accordingly, cooling the working fluid 116 within the hot cylinder 110 before beginning the compression phase reduces the amount of work needed to compress the working fluid 116 within the hot cylinder 110. In this way, the Stirling engine uses compression and expansion of the working fluid 116 to convert the heat supplied at the hot plate 102 into mechanical energy in the form of a moving swash plate 106.

In some embodiments, energy derived from the patient's thermal energy can assist or drive the Stirling engine by supplying at least a portion of the heat delivered to the working fluid 116 through the hot plate 102. In some embodiments, the pump system 100 can be incorporated into a portable wound dressing for use in TNP therapy. In at least one embodiment, a portable wound dressing for use in TNP therapy can include a pump system including a bio-thermic Sterling engine that extends operational duration of the portable wound dressing.

In some of the embodiments disclosed herein, the mechanical energy of the swash plate 106 can be used to generate a negative pressure for TNP therapy. In at least one embodiment, the swash plate 106 can generate a vacuum pressure by compressing an elastic member such as a spring, a bladder, or a foam sponge. In many embodiments, the pump system 100 can be configured so that the subsequent elastic recovery of the compressed elastic member generates a vacuum pressure, as described below.

In some embodiments, the pump system 100 can include a first bellows 124A. In at least one embodiment, the first bellows 124A can be disposed between the hot plate 102 and the swash plate 106. In some embodiments, the first bellows 124A can be disposed between the cold plate 104 and the swash plate 106. In some embodiments, movement of the swash plate 106 can compress the first bellows 124A between the swash plate 106 and the hot plate 110 or between the swash plate 106 and the cold plate 104. In many embodiments, the pump system 100 can include a plurality of first bellows 124A. In some embodiments, the pump system 100 can have a first bellows 124A disposed between the swash plate 106 and the cold plate 104 and another first bellows 124A disposed between the swash plate 106 and the hot plate 102.

In some embodiments, the first bellows 124A can be connected to an upstream directional valve 130 that can allow fluid to flow into the first bellows 124A while preventing fluid from flowing out of the first bellows 124A. In some embodiments, the first bellows 124A can be coupled to a downstream directional valve 136, that can allow fluid to flow out of the first bellows 124A while preventing fluid from flowing into the first bellows 124A.

In some embodiments, the first bellows 124A can be coupled to a vacuum line 126. In many embodiments, an upstream directional valve 130 can couple the first bellows 124A to the vacuum line 126. In some embodiments, the upstream directional valve 130 can allow fluid flow in the direction from the vacuum line 126 into the first bellows 124A and can restrict fluid flow in the direction from the first bellows 124A into the vacuum line 126. In many embodiments, the vacuum line 126 can have a distal end 132 that can be connected to the first bellows 124A and a proximal end 134 that can be fluidically coupled to the wound. In some embodiments, the proximal end 134 of the vacuum line 126 can be fluidically coupled to a wound facing surface 222 of a drape 220 that forms a seal over the wound (see FIG. 2). In at least one embodiment, the vacuum line 126 can fluidically couple to a space formed between the wound and the wound facing surface 222 of the drape 220. In some embodiments, the vacuum line 126 can include a trap 216 (see FIG. 2) that receives wound exudate from the wound and prevents the wound exudate from entering the first bellows 124A. In some embodiments, a layer of the wound dressing such as a layer of gauze can serve as the trap 216. In some embodiments, a canister can serve as the trap 216. In some embodiments, the wound exudate can be drawn into the first bellows 124A and then pumped out of the first bellows 124A and into an outflow line 142.

In some embodiments, the first bellows 124A can be fluidically coupled to a second bellows 124B by a bellows connecting line 140. In many embodiments, the bellows connecting line 140 can have directional valves 130, 136 that enable fluid to flow from the first bellows 124A to the second bellows 124B without allowing the fluid to flow in a retrograde direction (i.e., from the second bellows 124B to the first bellows 124A). In some embodiments, the second bellows 124B can be connected to an outflow line 142. In at least one embodiment, the second bellows 124B can be connected to an outflow line 142 having an outlet directional valve 137 that prevents fluid from flowing back from the outflow line 142 and into the second bellows 124B. In some embodiments, the pump system 100 can have a plurality of first and second bellows 124A, 124B. In at least one embodiment, the pump system 100 can have a first and second bellows 124A, 124B disposed between the cold plate 104 and the swash plate 106 and another first and second bellows 124A, 124B disposed between the hot plate 104 and the swash plate 106. In some embodiments, the swash plate 106 can generate a vacuum pressure using a plurality of first and second bellows 124A, 124B mounted onto only the cold plate 104, or onto only the hot plate 106, or onto both the cold plate 104 and the hot plate 106. In many embodiments, the first and second bellows 124A, 124B are thermally isolated from the outside environment.

In many embodiments, the heat added to the working fluid 116 can be used to generate a vacuum pressure. In some embodiments, heat added to the working fluid 116 within the hot cylinder 110 can cause the working fluid 116 within the hot cylinder 110 to expand, driving the swash plate 106 away from the hot plate 102. In some embodiments, a first bellows 124A can be disposed opposite the hot cylinder 110 and between the swash plate 106 and the cold plate 104 so that as the swash plate 106 moves away from the hot plate 102 the swash plate 106 compresses the first bellows 124A. In many embodiments, the first bellows 124A can have an outlet directional valve 137 that allows fluid to flow from the first bellows 124A into an outflow line 142 as the swash plate 106 compresses the first bellows 124A. In many embodiments, the first bellows 124A can have an upstream directional valve 130 that can allow fluid to flow into the first bellows 124A from a vacuum line 126 as the swash plate 106 moves away from the cold plate 104 causing the volume of the first bellows 124A to expand. In this way, pumping of gas through the first bellows 124A can be driven in anti-phase to the expansion of the hot cylinder 110. In some embodiments, the first bellows 124A can be elastic and the swash plate 106 can move away from the cold plate 104 as the first bellows 124A elastically recovers following compression of the first bellows 124A by the swash plate 106. In some embodiments, the swash plate 106 moves away from the cold plate 104 due to momentum imparted to the swash plate 106 during the expansion of the working fluid within the hot cylinder 110.

In some embodiments, a first bellows 124A can be disposed opposite the cold cylinder 112 and between the swash plate 106 and the hot plate 102 so that as the swash plate 106 moves away from the cold plate 104 the swash plate 106 compresses the first bellows 124A. In many embodiments, the first bellows 124A can have an outlet directional valve 137 that allows fluid to flow from the first bellows 124A into an outflow line 142 as the swash plate 106 compresses the first bellows 124A. In many embodiments, the first bellows 124A can have an upstream directional valve 130 that can allow fluid to flow into the first bellows 124A from a vacuum line 126 as the swash plate 106 moves toward the cold plate 104 causing the volume of the first bellows 124A to expand. In this way, pumping of gas through the first bellows 124A can be driven in anti-phase to the expansion of the cold cylinder 112. In some embodiments, the first bellows 124A can be elastic and the swash plate 106 can move away from the hot plate 102 as the first bellows 124A elastically recovers following compression of the first bellows 124A by the swash plate 106. In some embodiments, the swash plate 106 moves away from the hot plate 102 due to momentum imparted to the swash plate 106 during the expansion of the working fluid within the hot cylinder 110.

In many embodiments, the pump system 100 can have a regenerator 144. In some embodiments, the regenerator 144 can be disposed in series with the connecting line 114. In some embodiments, the working fluid 116 can flow through the regenerator 144 as the working fluid 116 passes through the connecting line 114. In many embodiments, the regenerator 144 can have a material that imposes a low impedance on the flow of the working fluid 116 when the working fluid 116 flows through the regenerator 144. In many embodiments, the regenerator 144 can maintain a temperature gradient, with the portion of the regenerator 144 closest to the hot cylinder 110 having a higher temperature than the portion of the regenerator 144 closest to the cold cylinder 112. In many embodiments, the regenerator 144 can accept heat from the working fluid 116 as the working fluid 116 flows from the hot cylinder 110 toward the cold cylinder 112. Similarly, in many embodiments the regenerator 144 can transfer heat to the working fluid 116 as the working fluid 116 moves from the cold cylinder 112 to the hot cylinder 110. In this way, the regenerator 144 may improve efficiency of the pump system 100 by reducing the loss of heat to the surroundings.

The pump systems 100 herein disclosed encompass a variety of configurations of the hot and cold cylinders 110, 112. For example, some embodiments of the pump system 100 can have two hot cylinders 110, two cold cylinders 112 and two connecting lines 114 that are arranged to establish two independent closed systems that can drive the swash plate 106. In at least one embodiment, the pump system 100 can have two independent closed systems (as discussed in the previous sentence) with one hot cylinder 110 being 180° circumferentially displaced on the hot plate 102 relative to the other hot cylinder 110. Similarly, some embodiments of the pump system 100 can have one cold cylinder 112 being 180° circumferentially displaced on the cold plate 104 relative to the other cold cylinder 112. In at least one embodiment of the pump system 100, the hot cylinder 110 can be fluidically connected to a cold cylinder 112 that is 90° circumferentially displaced on the cold plate 104 relative to the placement of the hot cylinder 110 on the hot plate 102. In some embodiments, the hot cylinder 110 can be fluidically connected to a cold cylinder 112 that is circumferentially displaced on the cold plate 104 relative to the placement of the hot cylinder 110 on the hot plate 102 by and angle other than 90°.

In some embodiments, at least a portion of the swash plate 106 can be formed as, or connected to, a traditional piston that moves within the hot and cold cylinders 110, 112. In some embodiments, the hot or cold cylinders 110, 112 can be made of an elastomeric material.

The pump systems 100 herein disclosed also encompass a variety of configurations of the first and second bellows 124A, 124B. In some embodiments, the first and second bellows 124A, 124B can be substantially linearly aligned with one another, running along a diameter of the hot or cold plates 102, 104. In at least one embodiment, the first bellows 124A can be 90° displaced circumferentially relative to the second bellows 124B. In many embodiments, the first bellows 124A can be disposed circumferentially relative to the second bellows 124B by an angle other than 90°. Additional sets of first and second bellows 124A, 124B, and additional sets of hot and cold cylinders 110, 112, can be fitted within a radius of the hot or cold plate 102, 104.

In many embodiments, the pump system 100 can include a set of first and second bellows 124A, 124B disposed on the cold plate 104 and a separate set of first and second bellows 124A, 124B disposed on the hot plate 102. In at least one embodiment, the set of bellows 124A, 124B disposed on the cold plate 104 can be 90° displaced circumferentially relative to the set of bellows 124A, 124B disposed on the hot plate 102. In some embodiments, the set of bellows 124A, 124B disposed on the cold plate 104 can be displaced circumferentially relative to the set of bellows 124A, 124B disposed on the hot plate 102 by an angle other than 90°. Additional sets of first and second bellows 124A, 124B, and additional sets of hot and cold cylinders 110, 112, can be arranged in series or in parallel. Series arrangements of the bellows or cylinders can generate greater pressure capability, while parallel arrangements of the bellows or cylinders can allow greater volumetric flow rates of the aspirated fluid. In some embodiments, the first and second bellows 124A, 124B can have different diameters or be located on different radii relative to the hot and cold cylinders 110, 112, enabling an increased pressure capability of the pump system 100 for a given heat differential.

Additional regenerators 144 can be used as well. In some embodiments, regenerators 144 from separate hot and cold cylinder sets can be thermally, but not fluidically, coupled, allowing heat transfer between the regenerators 144 but not allowing the working fluid 116 within the regenerators 144 to mix. In some embodiments, the regenerators 144 can include foam sections, with or without additional materials doping the foam sections, to alter heat transfer between the regenerator 144 and the working fluid 116.

In some embodiments, multiple versions of the pump system 100 can be mounted in an array. In some embodiments, certain pump systems 100 within the array can be powered by thermal input from the patient while other pump systems 100 can be powered by external heat sources. In some embodiments, the pump system 100 can include a first set of first and second bellows 124A, 124B, or a first set of hot and cold cylinders 110, 112, that are fluidically coupled to a second set of bellows or cylinders.

In some embodiments, the hot or cold plates 102, 104 can be made of foam or other flexible material, making the pump system 100 more flexible. In some embodiments, the flexible hot or cold plates 102, 104 may make the pump system 100 more flexible at the cost of lowering the efficiency of the pump system 100. In some embodiments, the hot and cold plates 102, 104, or the swash plate 106, can have a shape other than a disc (e.g., multi-armed cross, star, or ring). In some embodiments, the swash plate 106 may include multiple linked plates in place of a single plate. In some embodiments, one or more materials or layers maybe interposed between the swash plate 106 and the hot or cold plate 102, 104. In some embodiments, a dressing may incorporate the pump system 100 and one or more layers of woven or non-woven, foam, or superabsorber, or combination thereof.

The pump systems 100 herein disclosed encompass a variety of configurations of the first and second bellows 124A, 124B relative to the hot and cold cylinders 110, 112. By way of a non-limiting example, in at least one embodiment a first bellows 124A disposed on the hot plate 102 may be axially aligned with a cold cylinder 112 disposed on the cold plate 104 so that when a portion of the swash plate 106 moves to compress the first bellows 124A the cold cylinder 112 is contemporaneously expanded by the displacement of that portion of the swash plate 106 away from the cold plate 104. In many embodiments, the hot and cold cylinders 110, 112 may not be axially aligned with the first and second bellows 124A, 124B.

In some embodiments, the first and second bellows 124A, 124B can be disposed on the hot or cold plate 102, 104 at a same radial distance. In some embodiments, the first and second bellows 124A, 124B can be disposed on the hot or cold plate 102, 104 at a different radial distance. In some embodiments, the hot and cold cylinders 110, 112 can be disposed on the hot or cold plate 102, 104 at a same radial distance. In some embodiments, the hot and cold cylinders 110, 112 can be disposed on the hot or cold plate 102, 104 at a different radial distance. In some embodiments, the hot and cold cylinders 110, 112 can be arranged on the hot or cold plate 102, 104 at multiple radii around a center point 108, 109 of the hot or cold plate 102, 104. In some embodiments, the hot cylinders 110 can sit on a different Pitch Circle Diameter than the cold cylinders 112. In some embodiments, the first and second bellows 124A, 124B can sit on a different Pitch Circle Diameter than the hot or cold cylinders 110, 112.

In some embodiments, the hot plate 102 can have a direct thermal connection to the patient's skin. In some embodiments, the hot plate 102 can include a thermal connection to a separate heat pick-up (not shown) on the patient's skin. In some embodiments, a heating element 146 with or without additional thermal input from the patient's skin can supply heat to the hot plate 102. In some embodiments, the cold plate 104 can be passively cooled. In some embodiments, the cold plate 104 can include fins or other features that enhance heat transfer. In at least one embodiment, the cold plate 104 can be actively cooled by a fan or other element that increases heat transfer. In some embodiments, the working fluid 116 can be a fluid other than air.

In some embodiments, the cold cylinder 112 can be of a different shape or size compared to the hot cylinder 110. In some embodiments, the first bellows 124A can be of a different shape or size compared to the second bellows 124B. In at least one embodiment, the hot and cold cylinders 110, 112 can be of the same size and shape. In at least one embodiment, the first and second bellows 124A, 124B can be of the same size and shape. In at least one embodiment, the hot and cold cylinders 110, 112 can be the same size and shape as the first and second bellows 124A, 124B. In some embodiments, the hot and cold cylinders 110, 112 can be of a different shape or size compared to the first and second bellows 124A, 124B.

In some embodiments, the upstream and downstream directional valves 130, 136 can be controlled by a controller to control flow rate. In at least one embodiment, the upstream or downstream directional valves 130, 136 can include a material that changes shape when exposed to either temporary or continuous electrical potential (e.g., liquid crystals), allowing a complete close or a complete open of the upstream or downstream directional valve 130, 136 in additional to normal one-way functionality of the valve. In some embodiments, some or all of the upstream and downstream directional valves 130, 136 can have materials that change shape when exposed to pressure, allowing automatic control of the pressure generated by the pump system 100. In at least one embodiment, some or all of the upstream or downstream directional valves 130, 136 can have a material that swells when exposed to liquid, enabling the pumping system 100 to cease applying a negative pressure to the wound when the wound exudate begins to enter the first or second bellows 124A, 124B. In some embodiments, some or all of the upstream or downstream directional valves 130, 136 can include material that has a hysteresis in its shape with pressure, allowing a cyclic pressure to be applied to the wound.

In many embodiments, the first and second bellows 124A, 124B can be formed to have a planar profile. By way of a non-limiting example, some embodiments can have first and second bellows 124A, 124B formed as bubbles between two sheets of film or foam, similar to a bubble pack. In some embodiments, the swash plate 106 can use a shape other than a plate. In many embodiments, the swash plate 106 may have a shape such as a multi-armed cross, a star, or a ring. In some embodiments, the hot and cold plates 102, 104 can be made of foam or other flexible materials, making the pump system 100 more flexible. In some embodiments, the pump system 100 can be made more flexible at the cost of lowering the efficiency of the pump system 100.

In many embodiments, the pump system 100 herein disclosed can make the Stirling engine, including the crank mechanism, highly planar and make the pumping action direct, negating the complexity and energy loss inherent to an intermediate stage. In some embodiments, the use of larger and flatter the cylinders and bellows can enable greater pressure to be generated. In many embodiments, the planar configuration can make the pump system 100 suitable for an on-board dressing, particularly when the pump system 100 has an array of cylinders and bellows that can scale with the dressing size.

In many instances, the ratio of swept volumes of the hot and cold cylinders 110, 112 compared to the first and second bellows 124A, 124B can give a gearing, which limits the pressure that can be generated with a given heat differential. This means that the pump system 100 can be self-regulating and intrinsically safe, with no control electronics or systems. Against standard negative pressure would devices, the pump systems 100 herein disclosed can be made to run without external energy input, extending the operation of the device. In some embodiments, the continuous operation of the pump system 100 and its ability to be made large or arrayed means that the pumping action can be slow, enabling the flow rate of wound exudate to be comparatively low compared to a periodic running pump. In addition, the lack of mechanical clashing of components can make the pump system 100 quiet, producing low amounts of vibration.

In another embodiment of the heat-assisted pump system 200, a thermal acoustic engine (also referred to as a thermoacoustic engine) can be used to assist or to drive the generation of the vacuum pressure that is applied to the wound. In many embodiments, the pump system 200 can have a thermal acoustic engine that uses heat to generate a sound wave. The sound wave can then be used to establish a vacuum, as described below.

Figure 2:
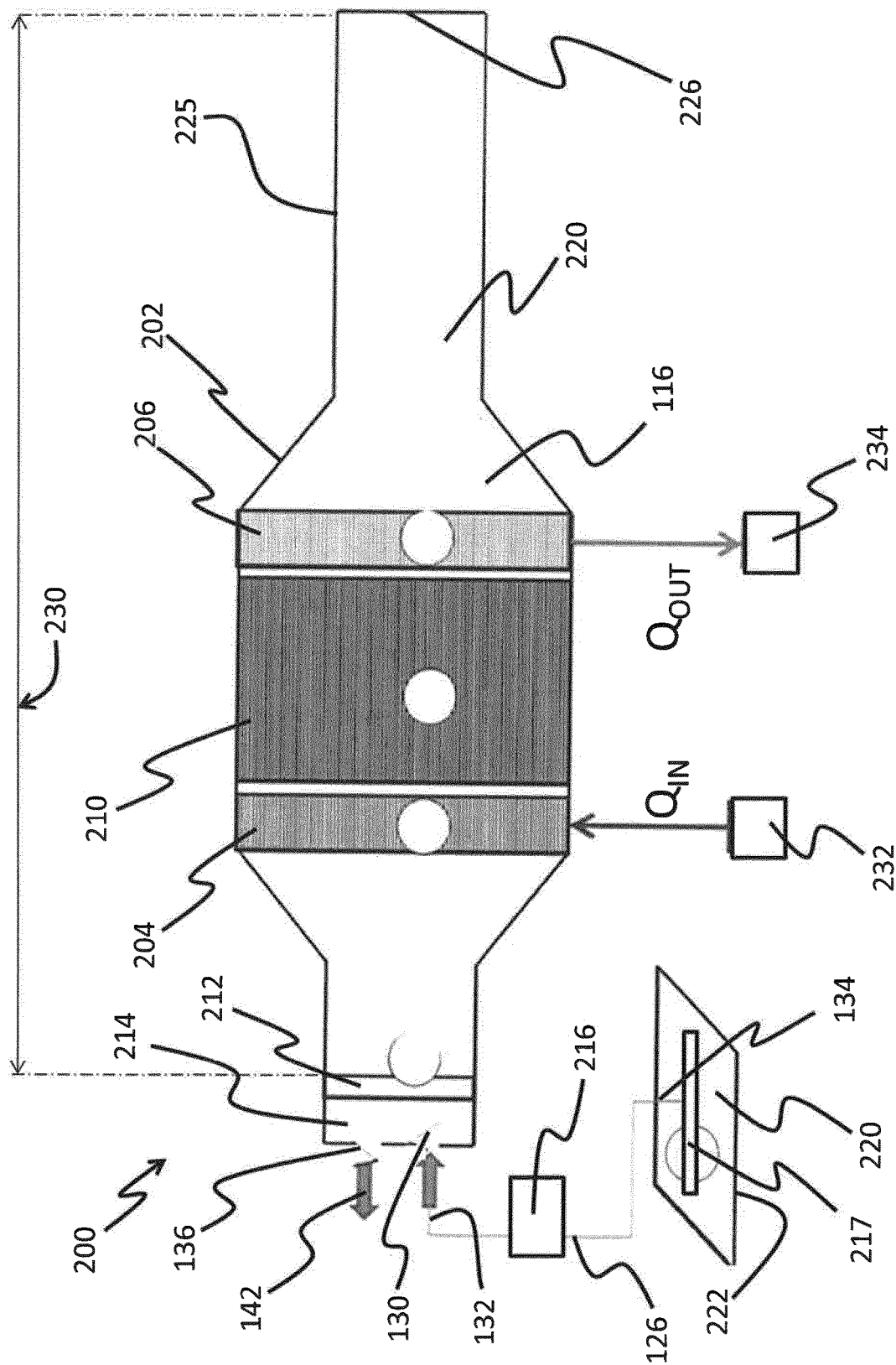
FIG. 2 is a schematic cross-sectional side view of a pump system comprising a thermoacoustic engine.

FIG. 2 depicts an embodiment of a TNP therapy wound dressing having a pump system 100 that can include a thermal acoustic engine. In some embodiments, a housing 202 can enclose a working fluid 116. In many embodiments, a hot heat exchanger 204 can be thermally coupled to a housing 202. In many embodiments, a cold heat exchanger 206 can be thermally coupled to the housing 202. In some embodiments, the housing 202 can be thermally coupled to both a hot heat exchanger 204 and a cold heat exchanger 206. In some embodiments, a stack 210 can be disposed within the housing 202. In at least one embodiment, the stack 210 can be disposed between the hot heat exchanger 202 and the cold heat exchanger 206.

In many embodiments, the stack 210 can include a porous material. In some embodiments, the stack 210 can establish a temperature gradient between the hot heat exchanger 204 and the cold heat exchanger 206. In at least one embodiment, the stack 210 can include a wire mesh. In some embodiments, the stack can be made of a material selected from the group consisting of metal, ceramic, or plastic. In many embodiments, the stack 210 can allow the working fluid 116 to pass through the stack with the stack imposing a low impedance to the movement of the working fluid 116. In many embodiments, the stack 210 can transfer heat to, or accepts heat from, the working fluid 116 as the working fluid 116 passes through the stack 210.

In many embodiments, heat can be added to the working fluid 116 through the hot heat exchanger 204 which can be thermally coupled to a heat source 232. Heat can be withdrawn from the working fluid 116 by the cold heat exchanger 206 which can be thermally coupled to a heat sink 234. In many embodiments, at least a portion of the heat added to the working fluid 116 can come from the patient. In at least one embodiment, the hot heat exchanger 204 can include a thermal pick up that can be coupled to the patient's skin.

As heat is added to the working fluid 116 at the hot heat exchanger 204, the working fluid 116 can expand, moving through the stack 210 toward the cold heat exchanger 206. The hotter working fluid 116 can pass its heat to a neighboring portion of working fluid 116 that is at a lower temperature. The flow of heat from the hotter working fluid 116 to the cooler working fluid 116 can reduce the temperature of the hotter working fluid 116, causing the hotter working fluid 116 to contract and move back toward the hot heat exchanger 204. As the fluid moves back toward the hot heat exchanger 204, the fluid can receive heat from a neighboring portion of working fluid 116 that is closer to the hot heat exchanger 204. In this way, the thermal energy generated by the heat source 212 can be transmitted through the working fluid 116 in a "bucket-chain-effect."

This "bucket-chain" manner of heat transfer within the working fluid 116 can cause the working fluid 116 to oscillate or vibrate between the hot heat exchanger 204 and the cold heat exchanger 206. As the working fluid 116 oscillates, it can move back and forth within the stack 210. Over time, the stack 210 can acquire a temperature gradient, with the portion of the stack 210 next to the hot heat exchanger 204 having a higher temperature than the portion of the stack 210 next to the cold heat exchanger 206. The temperature gradient of the stack 210 can enable the stack 210 to draw heat from the working fluid 116 as the working fluid 116 moves toward the cold heat exchanger 206 and to add heat to the working fluid 116 as the working fluid 116 moves toward the hot heat exchanger 204. In this way, the stack 210 can assist the "bucket-chain" manner of heat transfer within the working fluid 116.

The oscillating movement of the working fluid 116 can generate a similarly oscillating pressure field (i.e., a sound wave) within the working fluid 116. In many embodiments, the pumping system 200 can use the mechanical energy of the sound wave to create a vacuum pressure.

In some embodiments, the pump system 200 can have a diaphragm 212. In many embodiments, the diaphragm 212 can be enclosed within the housing 202. In at least one embodiment, the diaphragm 212 can be disposed at one end of the housing 202, with the diaphragm 212 being closer to the hot heat exchanger 204 than to the cold heat exchanger 206. In at least one embodiment, the diaphragm 212 can be fitted in a distal end 226 of the housing 202. In at least one embodiment, the diaphragm 212 can be flexible and can move in response to the sound wave generated by the thermal acoustic engine.

In some embodiments, the diaphragm 212 can be coupled to an antechamber 214. In at least one embodiment, the antechamber 214 can have an upstream directional valve 130 that can allow fluid to flow through the valve in a direction toward the antechamber 214 but not allow fluid to flow through the valve in a direction away from of the antechamber 214. In some embodiments, the antechamber 214 can have a downstream directional valve 136 that can allow fluid to flow through the valve in a direction away the antechamber 214 but not allow fluid to flow through the valve in a direction toward from of the antechamber 214. In at least one embodiment, the antechamber 214 can have both an upstream directional valve 130 and a downstream directional valve 136.

In some embodiments, the antechamber 214 can be fluidically coupled to a vacuum line 126. In at least one embodiment, the vacuum line 126 can be fluidically coupled to the antechamber 214 by an upstream directional valve 130. In many embodiments, the vacuum line 126 can have a distal end 132 that can couple to the antechamber 214 and a proximal end 134 that can be fluidically coupled to wound site. In at least one embodiment, the proximal end 134 of the vacuum line 126 can couple to a manifold 217 that can transmit to the wound the negative pressure generated by the pump system 200. In at least one embodiment, the vacuum line can have a trap 216 that can receive wound exudate from the wound and prevent the wound exudate from entering the antechamber 214. In some embodiments, the antechamber 214 can be coupled to an outflow line 142. In at least one embodiment, the outflow line 142 can be coupled to the antechamber 214 by a downstream directional valve 136.

In many embodiments, the diaphragm 212 can deflect when the sound wave in the working fluid 116 strikes the diaphragm 212. In some embodiments, deflection of the diaphragm 212 in a direction away from the stack 210 can cause the pressure within the antechamber 214 to increase, and deflection of the diaphragm 212 in a direction toward the stack 210 can cause the pressure within the antechamber 214 to decrease. In this way, the diaphragm 212 can transform the sound wave in the working fluid 116 to an oscillating pressure field within the antechamber 214.

In some embodiments, the antechamber 214 can have an upstream directional valve 130 that can open when the pressure in the antechamber 214 is reduced by movement of the diaphragm 212. In some embodiments, the antechamber 214 can have a downstream directional valve 136 that can close when the pressure in the antechamber 214 is reduced by movement of the diaphragm 212. In at least one embodiment, an upstream directional valve 130 that can open when the pressure in the antechamber 214 is reduced by the diaphragm 212 moving in a direction toward the stack 210 can couple the antechamber 214 to a vacuum line 126 fluidically coupled to a space disposed between the drape 220 and the wound. In at least one embodiment, movement of the diaphragm 212 can generate a vacuum pressure that is applied at the wound. In at least one embodiment, a vacuum pressure generated by the movement of the diaphragm 212 can be strong enough to pull wound exudate out of the wound and into a gauze layer of a wound dressing or into the vacuum line 126. In some embodiments, the pump system 200 may not have a diaphragm 212, with the sound wave generated in the working fluid 116 able to directly cause the upstream and downstream directional valves 130, 136 to open and close. In at least one embodiment, the diaphragm 212 can be omitted and air is pulled through the vacuum line 126 by the pressure of the sound wave directly opening and closing the upstream or downstream directional valve 130, 136.

In some embodiments, a distal portion 225 of the housing 202 can have a resonator 220 that can tune the vibration of the working fluid 116. In some embodiments, a distal face 226 of the housing 202 can be a distance 230 away from the diaphragm 212. In some embodiments, the distance 230 can be a multiple of the wavelength of the sound wave generated by the oscillating working fluid 116. In some embodiments, the distance 230 can be a full wavelength. In some embodiments, the distance 230 can be a half wavelength or a quarter wavelength of the sound wave generated by the oscillating working fluid 116.

The pump systems 200 disclosed herein encompass a variety of configurations. In some embodiments, the pump system 200 can be part of the dressing for a negative pressure wound therapy device. In at least one embodiment, the pump system 200 can be a separate unit of a negative pressure wound therapy device, the pump system 200 being connected to the dressing by a conduit. In many embodiments, the pump system 200 can constitute a portion of a portable wound dressing.

In at least one embodiment, the hot heat exchanger 204 can be coupled to the patient's skin. In some embodiments, the hot heat exchanger 204 can have a heat pick-up on the patient's skin. In some embodiments, thermal energy derived from the patient can supply the heat transferred to the working fluid 116 by the hot heat exchanger 204. In at least one embodiment, the hot heat exchanger 204 can be powered by an external heat source 232 other than the patient. In some embodiments, the hot heat exchanger 204 can be powered by both the patient and an external heat source 232.

In some embodiments, the cold heat exchanger 206 can be coupled to a heat sink 234. In many embodiments, the cold heat exchanger 206 can be a passive heat exchanger. In some embodiments, the cold heat exchanger 206 can have structures, such as fins or convection channels, that aid in the exchange of heat with the surroundings. In at least one embodiment, the cold heat exchanger 206 can have an active element, such as a fan, to aid in the exchange of heat with the surroundings.

In at least one embodiment, the working fluid 116 can be enclosed within the housing 202. In some embodiments, the housing 202 can be open to the surrounding environment, allowing at least a portion of the working fluid 116 to communicate with the surrounding environment. In some embodiments, the working fluid 116 can be a fluid other than air.

In some embodiments, the upstream and downstream directional valves 130, 136 can be located in positions other than at the end of the housing 202. In some embodiments, some, or none, or all, of the upstream and downstream directional valves 130, 136 can be controlled by a controller that controls flow rate of wound exudate out of the wound. In some embodiments, some, or none, or all of the upstream and downstream directional valves 130, 136 can have materials that change when exposed to either temporary or continuous electrical potential, allowing complete closed or open of valve in addition to normal one-way functionality. In some embodiments, some or all of the upstream and downstream directional valves 130, 136 can include materials that change shape when exposed to pressure, allowing automatic control of the pressure generated by the pump system 100. In some embodiments, some or all of the upstream and downstream directional valves 130, 136 can include material that has a hysteresis in its shape in response to pressure, allowing the pump system 200 to generate a cyclic pressure that can be applied to the wound. In some embodiments, the upstream and downstream directional valves 130, 136 can include material that swells on contact with liquid, allowing the pump system 200 to cease pumping action if the dressing becomes full.

In some embodiments, the stack 210 can be doped with additional materials such as foam sections. In some embodiments, corresponding housings 202 from multiple devices can be arrayed or linked together to operate in parallel. In some embodiments, a dressing incorporating the pump system 200 can have one or more layer of woven or nonwoven foam, or super-absorber, or a combination thereof.

In some embodiments, the hot heat exchanger 204 and cold heat exchanger 206 can be inverted relative to the stack 210 (i.e., the cold heat exchanger 206 can be interposed between the stack 210 and the diaphragm 212). In some embodiments, the diaphragm 212 can be interposed between the stack 210 and the distal end 226 of the housing 202. In some embodiments, multiple pump systems 200 can be mounted in an array. In some embodiments, the array of multiple pump systems 200 can be arranged in series or in parallel. In some embodiments, some pump systems 200 of the array can be powered by thermal input from the patient while other pump systems 200 of the array can be powered by external heat sources.

Figure 3A:
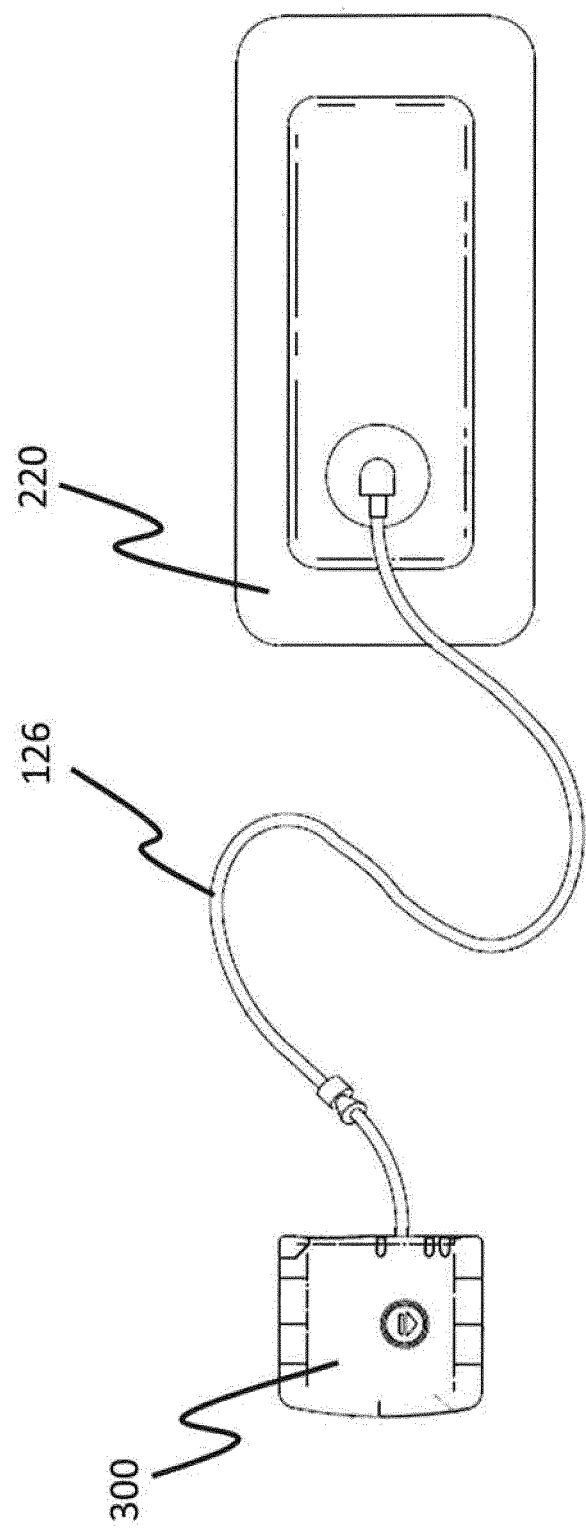
FIG. 3A is a schematic top view of a wound dressing having a pump system that can be located away from the wound site.
Figure 3B:
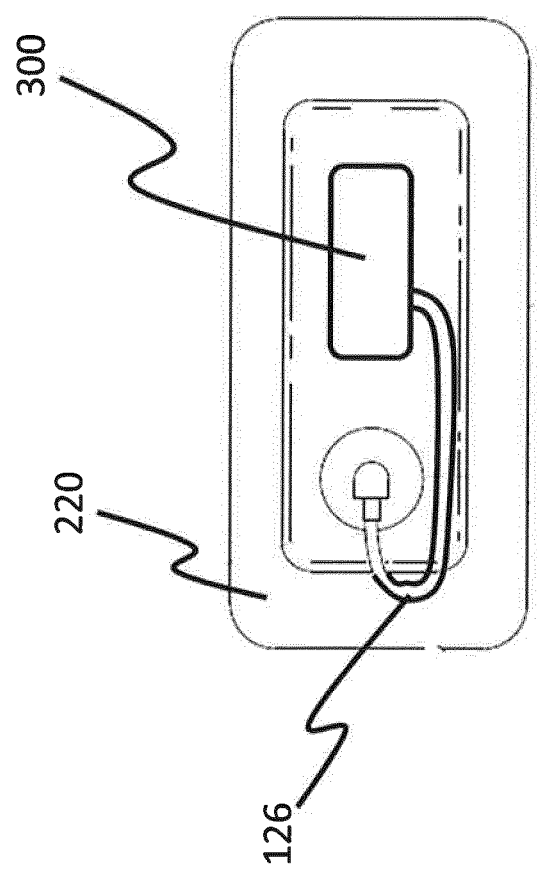
FIG. 3B is a schematic top view of a wound dressing having a pump system incorporated into the wound dressing.

The pump systems herein disclosed can utilized with a dressing for negative pressure wound therapy. As shown in FIG. 3A, a pump system 300, which may incorporate or comprise either the pump system 100 or 200 previously described, can be located away from the wound site with the negative pressure generated from the pump system 300 being delivered to the wound site by a vacuum line 126. In some embodiments, the pump system 300 can be thermally coupled to a portion of the patient's skin distant from the wound site. In some embodiments, the pump system 300 can be located at the wound site (see e.g., FIG. 3B). For example, the pump system 300 can be incorporated into the wound dressing 220. In at least one embodiment, the pump system 300 can be thermally coupled to the patient and located at the wound site. Further examples of wound dressings that may be utilized in combination with the pump systems described herein, and further embodiments of negative pressure wound therapy components that may be incorporated into, or used with, the apparatuses and methods described herein, are found in: PCT International Application No. PCT/IB2013/002060, filed Jul. 31, 2013; U.S. patent application Ser. No. 14/385,136, filed Sep. 12, 2014; U.S. patent application Ser. No. 14/209,907, filed Mar. 13, 2014, published as U.S. Pub. 2014/0316359; U.S. Pat. No. 8,905,985, issued Dec. 9, 2014; U.S. application Ser. No. 14/401,356, filed Nov. 14, 2014, published as U.S. Pub. 2015/0100045; and PCT International Application No. PCT/GB2011/000625, filed Apr. 21, 2011, published as WO 2011/135285, the entirety of each of which is hereby incorporated by reference, and are provided as Appendices A-F.

For example, some embodiments of wound dressings that may be utilized may comprise an absorbent layer for retaining wound exudate therein, such as the wound dressings available as part of the PICO system from Smith & Nephew. These negative pressure systems are preferably canister-less. Other examples include systems that use canisters to collect wound exudate, such as the RENASYS EZ and RENASYS GO systems available from Smith & Nephew. Such systems may include a wound packing material such as foam or gauze for placement into the wound, one or more adhesive drapes used to cover the wound and form a seal to skin surrounding the wound, and a port (such as SOFT PORT, available from Smith & Nephew) for connecting the drape to a source of negative pressure.

Figure 4A:
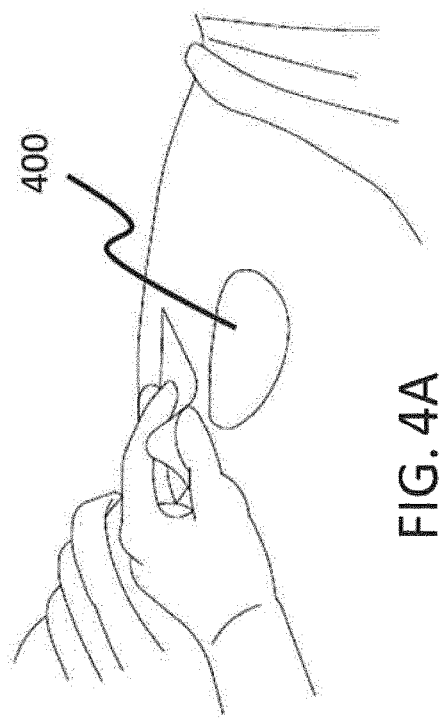
FIG. 4A illustrates a step of preparing the skin near a wound site to receive a wound dressing.
Figure 4C:
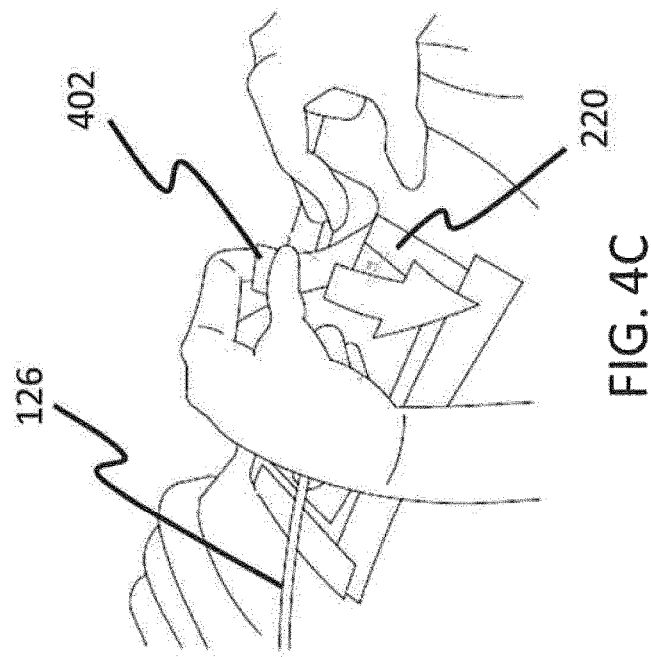
FIG. 4C illustrates a step of securing a wound dressing over a wound.
Figure 4B:
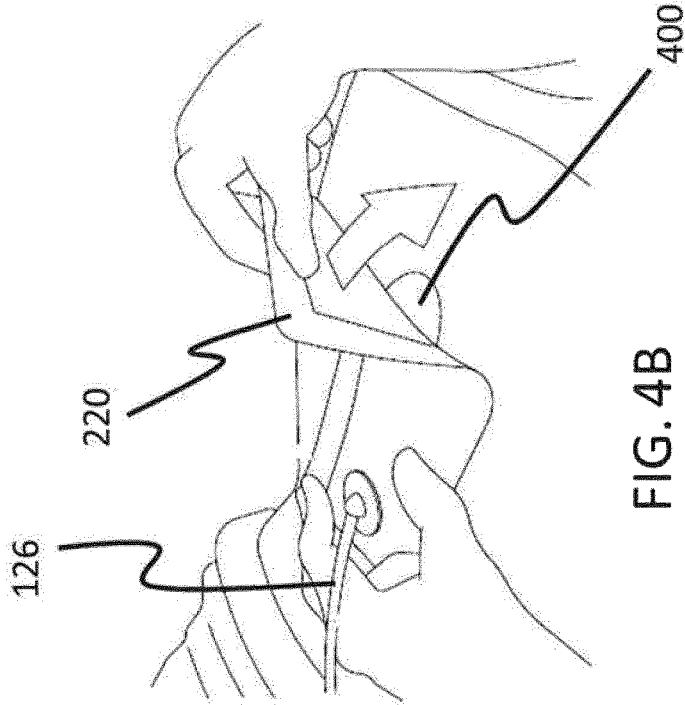
FIG. 4B illustrates a step of positioning a wound dressing over a wound.

FIGS. 4A-C depict a non-limiting example of a method of use of a wound dressing incorporating a pump system as disclosed herein for treatment of a wound with negative pressure wound therapy. The skin of the patient near the wound 400 can be prepared to receive the wound dressing (see e.g., FIG. 4A). The wound dressing can be laid over the wound 400 so that the drape or backing layer 220 of the wound dressing covers the wound 400 (see e.g., FIG. 4B). The wound dressing can be secured to the patient's skin by an adhesive tape 402, and/or it may have an adhesive layer on an underside thereof. In some embodiments, the wound dressing can form a substantially fluid-tight seal that allows a negative pressure generated by the pump system 100, 200 to be applied to the wound 400 through a vacuum line 126.

Although the thermal differential can be low between body heat and the environment, operation of the pump system 100 at approximately 0.5% efficiency in some embodiments can be enough to hold a negative pressure of 80 millimeters of mercury. In many embodiments, the pump system 100 can operate specifically by generating a defined frequency determined by its geometry, allowing the pump system 100 to be tuned to generate a sound wave having a frequency that disturbs the patient least.

The above presents a description of modes contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of this invention.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy system, comprising:
   a wound dressing configured to form a seal over a wound site of a patient; and
   a pump system configured to be in fluid communication with the wound dressing, the pump system further comprising:
   a housing; and
   a negative pressure source;
   wherein:
   the negative pressure source comprises a plurality of bellows each configured to move from a compressed position to an expanded position;
   the negative pressure source further comprises a pump actuator comprising a swash plate in contact with each of the plurality of bellows;
   the swash plate is configured to tilt back and forth about only one axis;
   the pump system is configured such that a tilting of the swash plate back and forth about only one axis moves the plurality of bellows at least from the expanded position to the compressed position;
   a vacuum pressure is generated by compressing the plurality of bellows into the compressed position and a subsequent recovery of the plurality of bellows from the compressed position to the expanded position generates the vacuum pressure within the wound dressing; and
   the pump system is incorporated into the wound dressing to form a single unit.

2. The negative pressure wound therapy system of claim 1, further comprising a first directional valve between the wound dressing and the plurality of bellows, wherein the first directional valve is configured to allow fluid flow in the direction from the wound dressing into the plurality of bellows and to restrict fluid flow in the direction from the plurality of bellows into the wound dressing.

3. The negative pressure wound therapy system of claim 2, wherein the pump system further comprises a second directional valve, wherein the second directional valve comprises an exhaust valve.

4. The negative pressure wound therapy system of claim 3, further comprising a vacuum line fluidically connected to a space disposed between the wound dressing and the wound site.

5. The negative pressure wound therapy system of claim 4, wherein the first directional valve couples the plurality of bellows to the vacuum line.

6. The negative pressure wound therapy system of claim 3, wherein the first directional valve is fluidly coupled to the plurality of bellows and the second directional valve is fluidly coupled to the plurality of bellows.

7. The negative pressure wound therapy system of claim 1, further comprising a fluid trap configured to receive wound exudate from the wound and prevent wound exudate from entering at least one of the plurality of bellows.

8. The negative pressure wound therapy system of claim 7, wherein the fluid trap comprises a canister.

9. The negative pressure wound therapy system of claim 1, further comprising a filter configured to prevent passage of liquids toward the pump system.

10. The negative pressure wound therapy system of claim 1, the wound dressing further comprising one or more dressing layers, wherein the one or more dressing layers comprise one or more of a woven or non-woven material, a foam, or an absorbent material.

11. The negative pressure wound therapy system of claim 1, the wound dressing further comprising an absorbent layer configured to retain wound exudate within the wound dressing.

12. The negative pressure wound therapy system of claim 1, wherein the pump actuator comprises a canted surface configured to contact the plurality of bellows and to move the plurality of bellows at least from the expanded position to the compressed position.

13. A negative pressure wound therapy system, comprising:
   a wound dressing configured to form a seal over a wound site of a patient; and
   a pump system configured to be in fluid communication with the wound dressing, the pump system further comprising:
      a housing; and
      a negative pressure source;
   wherein:
      the negative pressure source comprises one or more bellows configured to move from a compressed position to an expanded position and a pump actuator comprising a canted swash plate in contact with the one or more bellows and configured to move the one or more bellows at least from the expanded position to the compressed position by tilting back and forth about only one axis;
      a vacuum pressure is generated by compressing the one or more bellows into the compressed position and a subsequent recovery of the one or more bellows from the compressed position to the expanded position generates the vacuum pressure within the wound dressing; and
      the pump system is incorporated into the wound dressing to form a single unit.

14. The negative pressure wound therapy system of claim 13, further comprising a first directional valve between the wound dressing and the one or more bellows, wherein the first directional valve is configured to allow fluid flow in the direction from the wound dressing into the one or more bellows and to restrict fluid flow in the direction from the one or more bellows into the wound dressing.

15. The negative pressure wound therapy system of claim 14, wherein the pump system further comprises a second directional valve, wherein the second directional valve comprises an exhaust valve.

16. The negative pressure wound therapy system of claim 15, further comprising a vacuum line fluidically connected to a space disposed between the wound dressing and the wound site.

17. The negative pressure wound therapy system of claim 16, wherein the first directional valve couples the one or more bellows to the vacuum line.

18. The negative pressure wound therapy system of claim 13, wherein the negative pressure source comprises at least two bellows.

* * * * *